United States Patent [19]

Mahn et al.

[11] Patent Number: 4,725,612
[45] Date of Patent: Feb. 16, 1988

[54] SYNERGISTIC MICROBIOCIDAL COMPOSITIONS CONTAINING A MIXTURE OF A BICYCLIC POLYOXYMETHYLENE OXAZOLIDINE AND A 1,2-BENZISOTHIAZOLIN-3-ONE

[75] Inventors: Frederick R. Mahn, Verona; Lora J. Bogdany; Joseph J. Baron, Morris Plains; Edward G. Knapick; Edward M. Antonucci, both of Randolph, all of N.J.

[73] Assignee: Drew Chemical Corporation, Boonton, N.J.

[21] Appl. No.: 75,907

[22] Filed: Jul. 20, 1987

Related U.S. Application Data

[63] Continuation-in-part of Ser. No. 894,310, Aug. 6, 1986, abandoned.

[51] Int. Cl.$^4$ .................. A01N 43/76; A01N 43/80
[52] U.S. Cl. .................. 514/373; 514/375
[58] Field of Search .................. 514/373, 375

[56] References Cited

U.S. PATENT DOCUMENTS 3,065,123 11/1962 Hinton et al. .................. 514/373
4,135,945 1/1979 Buono et al. .................. 106/308 N Primary Examiner—Allen J. Robinson
Attorney, Agent, or Firm—Walter H. Schneider

[57] ABSTRACT

A synergistic microbiocidal composition for inhibiting bacterial growth comprising Component (1) having the formula:

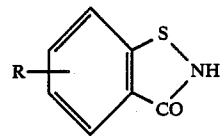

in which R represents hydrogen or a halogen atom, and alkali ammonium and amine salts thereof; and Component (2) having the formula:

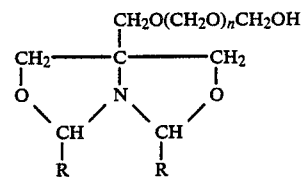

in which each R represents hydrogen, an alkyl of 1-6 carbons, phenyl, halophenyl or $-(CH_2O)_mCH_2OH$ in which m is 0-2 and n is 0-4; Component 1/Component 2 being in a weight ratio of at least 1:1.

2 Claims, No Drawings

SYNERGISTIC MICROBIOCIDAL COMPOSITIONS CONTAINING A MIXTURE OF A BICYCLIC POLYOXYMETHYLENE OXAZOLIDINE AND A 1,2-BENZISOTHIAZOLIN-3-ONE

This application is a continuation-in-part of application Ser. No. 894,310 filed Aug. 6, 1986, now abandoned.

BACKGROUND OF THE INVENTION

1. Field of the Invention

The present invention relates to inhibiting the growth of bacteria in various industrial environments. More particularly, the present invention relates to an improved microbiocidal composition and its method of use. Still more particularly, the present invention relates to a synergistic microbiocidal composition, and its method of use, the composition comprising a combination of a 1,2-benzisothiazolin-3-one and a bicyclic polyoxymethyleneoxazolidine.

2. Description of the Prior Art

The presence of organic materials in the manufacture and/or use of various aqueous systems such as latices, adhesives, paints, coatings, mineral slurries and the like renders them susceptible to deterioration by virtue of exposure to bacteria and other microorganisms existing in the particular environment. It is, therefore, a conventional practice to seek to inhibit the microbial deterioration of such systems by incorporating therein any of various materials or combinations of materials that are characterized by having antibacterial activity.

Numerous materials have been found to possess such antibacterial activity among which are various polyoxymethyleneoxazolidines as disclosed in U.S. Pat. No. 4,135,945 and various 1,2-benzisothiazolin-3-ones as disclosed in U.S. Pat. No. 3,065,123.

SUMMARY OF THE INVENTION

It is a principal object of this invention to provide an improved microbiocidal composition. It is a further object of this invention to provide an improved microbiocidal composition that is storage stable, and which is compatible with a variety of systems susceptible to biocidal degeneration thereby permitting its use without objectionable and/or unacceptable by-product odor, discoloration, thickening and the like. A further object of this invention is to provide an improved microbiocidal composition that is cost effective, i.e., performs effectively on the basis of its cost per unit weight and duration of its effectiveness on the treated system. Another object of this invention is to provide an improved method of inhibiting bacterial growth in a variety of systems used in industry and commerce.

DESCRIPTION OF THE PREFERRED EMBODIMENT

These various objects have been met in accordance with the present invention by a composition comprising (1) a 1,2-benzisothiazolin-3-one in combination with (2) a bicyclic polyoxymethyleneoxazolidine.

In accordance with the present invention, Component (1) of the composition is represented by the formula:

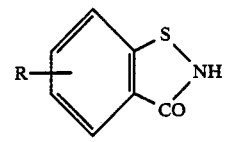

in which R represents hydrogen or a halogen atom, and alkali metal, ammonium or amine salts of such 1,2-benzisothiazolin-3-ones. The preferred compound for use in the synergistic composition of this invention is 1,2-benzisothiazolin-3-one.

Component (2) of the composition of the present invention is represented by the formula:

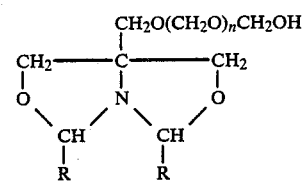

in which each R represents H, an alkyl of 1–6 carbons, phenyl, halophenyl or —$(CH_2O)_mCH_2OH$ in which m is 0–2 and n is 1–4.

The preferred bicyclic polyoxymethyleneoxazolidine for use in the composition of this invention comprises a mixture of:
(a) 35% 5-hydroxymethyl-1-aza-3,7-dioxabicyclo-(3.3.0)octane,
(b) 49% 5-hydroxymethoxymethoxymethyl-1-aza-3,7-dioxabicylco-(3.3.0)octane, and
(c) 16% 5-hydroxymethylpoly[oxymethylene($C_2$:74%; $C_3$:21%; $C_4$:4%; $C_5$:1%)]-1-aza-3,7-dioxabicyclo-(3.3.0)octane.

In the practice of the invention, the composition is used in a ratio of Component (1) to Component (2) of at least 1:1 by weight, since compositions in which the ratio is less than this have been found to be unstable. The ratio of components may be as high as 10:1, or higher, but will normally be used in a range of 1–5:1, a preferred ratio being about 3:1.

The composition can be employed in the form of a dilute aqueous or non-aqueous solution and can be added to the aqueous system to be treated in any conventional way in an amount effective to inhibit microorganism growth. Generally, the effective concentration will range from as little as 100 ppm to as much as 5000 ppm depending upon the nature of the system being treated. Usually, a concentration on the order of 500–200 ppm will be found adequate.

In order to demonstrate the synergistic microbiocidal activity of the composition of this invention, the following example was conducted. All parts are by weight unless otherwise noted.

EXAMPLE

An unpreserved sample of styrene-butadiene-vinylidene chloride (SBVC) latex was analyzed for microbial content before being utilized for preservation evaluation according to the invention. It was determined that the latex sample was free of contamination.

The uncontaminated, unprotected SBVC latex was divided into 50 gr. aliquots and dosed with the microbiocide composition of this invention as reported in the following Table. Each of Components 1 and 2 was also separately tested as microbiocides while two aliqouts remained untreated to serve as controls.

The challenged inoculum was a pooled suspension of microorganisms comprising the bacteria species Pseudomonas, Bacillus and Penicillium, that had been grown from contaminated latex material. All of the samples were challenged on a weekly basis for 4 weeks with 0.10 ml. of the pooled suspension containing at least $10^6$ organisms per ml. Following 72 hours of room temperature incubation, a one ml. quantity of each sample was transferred to 20 ml. of tryptic soy broth (TSB). The TSB tubes were incubated at room temperature for 24 hours and streaked onto TGE plates for growth bacteria. After 48 hours incubation at room, the plates were read and graded according to the description following the Table.

The tested composition was the preferred composition referred to above in which Component (1) was 1,2-benzisothiazolin-3-one and Component (2) was a mixture of bicyclic polyoxymethyleneoxazolidines comprising components (a), (b) and (c) identified above. Component (1) was obtained from ICI Americas under the trademark Proxel® GXI as a solution in dipropylene glycol containing 17% active ingredient. Component (2) was obtained from Nuodex, Inc. under the trademark Nuosept® 95 as an aqueous solution containing 50% active ingredient. The composition was adjusted to an active ingredient content of 10% while Components (1) and (2) were adjusted to an active ingredient content of 20% for testing individually. Results appear in the Table.

TABLE

| Biocide | Ratio | PPM | Weekly Growth Rate* | | | |
|---|---|---|---|---|---|---|
| | | | 1 | 2 | 3 | 4 |
| Components 1 and 2 | 1:1 | 1000 | — | +1 | +1 | +1 |
| | | 2000 | — | — | — | — |
| | | 4000 | — | — | — | — |
| Components 1 and 2 | 3:1 | 1000 | — | — | — | — |
| | | 2000 | — | — | — | — |
| | | 4000 | — | — | — | — |
| Component 1 | | 500 | +2 | +3 | +3 | +3 |
| | | 1000 | +2 | +2 | +3 | +3 |
| | | 2000 | +1 | +1 | +2 | +2 |
| Component 2 | | 500 | +1 | +1 | +1 | +2 |
| | | 1000 | — | +1 | +1 | +2 |
| | | 2000 | — | +1 | +1 | +1 |
| Control #1 | | | +2 | +4 | +4 | +4 |
| Control #2 | | | +4 | +4 | +4 | +4 |

*The rating system for microbial growth on streaked, prepoured agar plates is as follows:

| Growth rate | Description |
|---|---|
| — | No growth; zero colonies |
| +1 | Maximum of 15 total colonies with no more than 5 of these having diameters of ⅛ inch |
| +2 | Sporadic growth on ½ total streaked area, remaining ½ area relatively clear; maximum of 20 total colonies with no more than 6 of these having diameters greater than ⅛ inch |
| +3 | Dense growth on ⅝-¾ of streaked area; minor colonies too numerous to count; 20 or more major colonies having diameters of ⅛ inch or larger |
| +4 | Uniform, dense growth over entire streaked area; colonies pinhead size or larger |

Reference in the disclosure to details of specific embodiments is not intended to restrict the scope of the appended claims, which themselves recite those features regarded as essential to the invention.

We claim:

1. A microbiocidal composition comprising a synergistic mixture the first component of which is 1,2-benzisothiazolin-3-one and the second component of which is a bicyclic polyoxymethyleneoxazolidine comprising a mixture of (a) 35% 5-hydroxymethyl-1-aza-3,7-dioxabicyclo-(3.3.0)-octane, (b) 49% 5-hydroxymethylmethoxy-1-aza-3,7-dioxabicyclo-(3.3.0)-octane, and (c) 16% 5-hydroxymethylpoly[oxymethylene($C_2$:74%; $C_3$:21%; $C_4$:4%; $C_5$:1%)]-1-aza-3,7-dioxabicyclo-(3.3.0)-octane, said first and second components being in a ratio of 1–3:1 by weight.

2. A method for inhibiting the growth of bacteria in an aqueous system which comprises adding to said system an amount of a microbiocidal composition according to claim 1 effective to inhibit the growth of bacteria.

* * * * *